United States Patent
Hasegawa et al.

(10) Patent No.: US 9,658,163 B2
(45) Date of Patent: *May 23, 2017

(54) ASSAYING SUBSTRATE WITH SURFACE-ENHANCED RAMAN SCATTERING ACTIVITY

(75) Inventors: Yuki Hasegawa, Himeji (JP); Katsuyuki Hasegawa, Himeji (JP)

(73) Assignee: MYTECH CO., LTD., Himeji-Shi, Hyogo (JP)

( * ) Notice: Subject to any disclaimer, the term of this patent is extended or adjusted under 35 U.S.C. 154(b) by 1248 days.

This patent is subject to a terminal disclaimer.

(21) Appl. No.: 13/255,071

(22) PCT Filed: Mar. 4, 2010

(86) PCT No.: PCT/JP2010/053509
§ 371 (c)(1), (2), (4) Date: Jan. 17, 2012

(87) PCT Pub. No.: WO2010/101209
PCT Pub. Date: Sep. 10, 2010

(65) Prior Publication Data
US 2012/0115245 A1    May 10, 2012

(30) Foreign Application Priority Data
Mar. 4, 2009 (JP) ................................. 2009-051105
Jul. 22, 2009 (JP) ................................. 2009-171354

(51) Int. Cl.
G01N 33/553 (2006.01)
G01N 21/65 (2006.01)
G01N 33/543 (2006.01)
B82Y 15/00 (2011.01)

(52) U.S. Cl.
CPC ............ G01N 21/658 (2013.01); B82Y 15/00 (2013.01); G01N 33/54346 (2013.01); G01N 33/553 (2013.01)

(58) Field of Classification Search
CPC ........ C12Q 2563/155; C12Q 2565/632; B82Y 15/00; G01N 21/658
See application file for complete search history.

(56) References Cited

U.S. PATENT DOCUMENTS

| | | | | |
|---|---|---|---|---|
| 5,376,556 A | * | 12/1994 | Tarcha | G01N 21/658 435/968 |
| 6,989,897 B2 | * | 1/2006 | Chan | C12Q 1/6825 356/244 |
| 7,019,828 B2 | * | 3/2006 | Su | G01N 21/658 356/301 |
| 9,139,907 B2 | * | 9/2015 | Hasegawa | G01N 21/658 |
| 2008/0003576 A1 | * | 1/2008 | Zhang et al. | 435/6 |
| 2009/0201496 A1 | * | 8/2009 | Lee | G01N 21/658 356/301 |
| 2011/0026019 A1 | * | 2/2011 | Tyagi et al. | 356/301 |

FOREIGN PATENT DOCUMENTS

| | | |
|---|---|---|
| JP | 7-146295 A | 6/1995 |
| JP | 10-160737 A | 6/1998 |
| JP | 11-61209 A | 3/1999 |
| JP | 2007-198933 A | 8/2007 |
| JP | 2008-96189 A | 4/2008 |
| WO | 2007/060989 A1 | 5/2007 |
| WO | 2008/010442 A1 | 1/2008 |

OTHER PUBLICATIONS

Yuling Wang, Hongjun Chen and Erkang Wang, "Facile fabrication of gold nanoparticle array for efficient surface-enhanced Raman scattering", Nanotechnology, 19 (2008) 105604.*
Kwan Kim and Hyun Sook Lee, "Effect of Ag and Au nanoparticles on the SERS of 4-Aminobenzenethiol assembled on powdered copper", J. Phys. Chem. B, 2005, 109, 1829-18934.*
International Search Report issued for corresponding PCT/JP2015/053509 application.
Watabe et al., "Kikinzoku Nano Ryushi Gosei Ho no Kaihatsu to Sono Oyo", Annual Report of Research Institute for Science and Technology, 2006, No. 14; pp. 85 to 90.
S. Nie and S. R. Emory, Science. 275, 1102 (1997).
K.C. Grabar, P.C. Smith, M.D. Musick, J.A. Davis, D.G. Walter, M.A. Jackson, A.P. Guthrie and M.J. Natan, J. Am. Chem, Soc., 118, 1148 (1996).
R.M. Bright, M.D. Musick and M. H. Natan, Lanamuir, 14, 5695 (1998).

* cited by examiner

Primary Examiner — Chris L Chin
(74) Attorney, Agent, or Firm — IP Business Solutions, LLC

(57) ABSTRACT

A metal substrate obtained by agglomerating 5 nm to 100 nm metal nano-particles (including clusters) having SERS activity on a metal substrate having a lower electrode potential (higher ionization tendency) than the electrode potential of the metal nano-particles, and fixing the metal nano-particles in an optimally agglomerated state that acts as hot sites, when a detection specimen is adsorbed in a non-dried state, and a predetermined laser light is irradiated, the surface enhanced Raman scattered (SERS) light of antigen detection specimen can be detected by surface Raman resonance in an optimally agglomerated state.

2 Claims, 5 Drawing Sheets

ASSAYING SUBSTRATE WITH SURFACE-ENHANCED RAMAN SCATTERING ACTIVITY

TECHNICAL FIELD

The present invention relates to a measuring substrate having surface enhanced Raman scattering (hereinafter referred to simply as SERS) activity with a high reproducibility and a method of measuring surface enhanced Raman light using the same.

BACKGROUND ART

In recent years, there has been an increasing need for measuring a single molecule (for example, protein) in a cell and clarifying the mechanism of diseases or life phenomena in the bio field centered on life sciences. In order to satisfy such a need, an ultrasensitive analysis technique, with which cells can be observed alive and unlabeled, has become indispensable.

Currently, as a detecting method in the bio field, surface enhanced Raman spectroscopy is gaining attention as an ultrasensitive analyzing method which combines "spectroscopy using the Raman effect" and "the enhancing effect of light on a metal surface," and is used to identify substances and the like. The Raman effect refers to a phenomenon in which, when light enters a substance, the scattered light includes light having different wavelengths from the wavelength of the incident light (inelastic scattering). The scattered light at this time is called Raman scattered light. Raman spectroscopy is known in which, since the difference in energy between the light scattered by the Raman effect and the incident light corresponds to the energy at the vibration level, rotation level, or electron level of a molecule or crystal in a substance, and the molecule or crystal has an intrinsic vibration energy in accordance with the structure, chemical species are identified from spectra, and the quantity of a target substance is determined from the intensity of the scattered light using a phenomenon in which the molecule or crystal is modulated to light in which the molecular intrinsic energy state is reflected, by using a laser which is a monochromatic light. However, since the sensitivity of Raman spectroscopy is intrinsically low, the Raman spectroscopy is not appropriate for analysis of a small amount of specimen.

On the other hand, in a metal nano-particle, plasmon, which, is a phenomenon in which free electrons present on a metal surface collectively vibrate, occurs on the metal surface, and this surface plasmon is coupled with an optical electric field in a visible light to near-infrared region, thereby significantly enhancing the electric field on the surface of the metal nano-particle. Surface enhanced Raman spectroscopy has come to gain attention since use of this surface plasmon resonance irradiates laser light to a molecule adsorbed to the surface of the metal nano-particle, and drastically enhances the Raman scattered light that is generated from the adsorbed molecule. One of the surface enhanced Raman spectroscopies that are carried out is SERS measurement in which the fact that a substance is adsorbed to the surface of a noble metal electrode, such as gold and silver, or colloid, and the vibration spectrum is enhanced in comparison to a single molecule is used (PTL 1).

This SERS measurement is a useful method for the structural analysis of a small amount of a substance; however, currently, this method is told that it is necessary to accumulate fine particles of a noble metal, such as silver and gold, having a size of about several tens of nm to several hundreds of nm on a glass substrate, and, in the past, it was necessary to synthesize colloid particles of silver or gold in solution, and fix them on a substrate modified by a lysine or cyan (NPL 1, 2, and 3, and PTL 2). Particularly, in PTL 2, a so-called drop & dry method is employed in which colloids that have been prevented from agglomerating are gelatinized, coated, and dried so as to produce a substrate, and form a main stream.

CITATION LIST

Patent Literature
[PTL 1] JP-A-7-146295
[PTL 2] JP-A-11-61209
Non Patent Literature
[NPL 1] S. Nie and S. R. Emory, Science. 275, 1102 (1997)
[NPL 2] K. C. Grabar, P. C. Smith, M. D. Musick, J. A. Davis, D. G. Walter, M. A. Jackson, A. P. Guthrie and M. J. Natan, J. Am. Chem, Soc., 118, 1148 (1996)
[NPL 3] R. M. Bright, M. D. Musick and M. H. Natan, Lanamuir, 14, 5695 (1998)

SUMMARY OF INVENTION

Technical Problem

However, in the drop & dry method, measurement takes time, a test sample needs to be detected in a non-dried state immediately after being dropped (drop in situ) in order to rapidly and precisely detect the test sample, and it is said that the drop & dry method is still inadequate at carrying out an analysis of extremely small amounts of chemical species in gas phase, such as a diagnosis of a disease.

The reasons are as follows: while a silver nano-particle has a strong activity in solution, when the silver nano-particle is dried, the size of the nano-particle is changed, and the activity is lowered. In addition, a gold nano-particle is stable in the atmosphere, but intrinsically has a lower SERS activity than silver, and therefore the density of the gold nano-particle that can be fixed on a glass substrate in a nano-particle dispersed liquid is extremely small.

Considering the fact that places at which an electric field enhancing effect due to surface plasmon resonance is significantly generated (hot sites) are significantly generated mainly between adjacent metal nano-particles or clusters, at the front end of an edge shape, and the like, an object of the invention is to provide a measuring substrate with which metal nano-particles are formed while the agglomeration state of the metal nano-particles, which act as the hot sites, is controlled, and a specimen can be detected immediately after being dropped, and a measuring method using the same.

Solution to Problem

The invention has been made in consideration that a silver nano-particle or clusters dispersed liquid immediately starts to be agglomerated and fixed on a copper or copper alloy substrate so as to be in a state in which instant surface enhanced Raman scattered light measurement is possible, and the invention is a substrate for surface enhanced Raman scattered light measurement in which a dispersed liquid including 100 ppm to 5000 ppm of nano-particles (including clusters), which have a particle diameter of 100 nm or less, of a metal having SERS activity is agglomerated on a metal substrate having a higher electrode potential (lower ionization tendency) than the electrode potential of the metal, and agglomeration is stopped in a desired agglomerated state, whereby agglomerated regions form hot sites for surface enhanced Ramen scattering (SERS) measurement.

According to the invention, the metal nano-particles or clusters are fixed on the metal substrate in the process of agglomeration from the metal nano-particle or cluster dispersed liquid, the attachment strength is so strong that an agglomerated film is not easily separated even when the dispersed liquid is wiped off in the agglomeration process, and agglomeration can be almost stopped at that point of time. Therefore, it is possible to disperse a detection specimen in the metal nano-particle dispersed liquid, and irradiate laser light while the dispersed liquid is dropped and agglomerated on a metal substrate, but measurement of Raman scattered light, which is optimized by dropping a detection solution in the following substrate, becomes possible by dropping only a metal nano-particle dispersed liquid on a metal substrate, and timely wiping off and drying the metal nano-particle dispersed liquid in the agglomeration process, thereby preparing a measuring substrate on which agglomerated regions for hot sites of the metal nano-particle which is effective for Raman scattered light detection.

The measuring substrate preferably has a plurality of hot sites in which two or more metal nano-particles or clusters are chained and adjusted to have an inter-particle distance of at least 10 nm or less per unit area. Here, the metal nano-particle refers to a metal particle having a particle diameter of 100 nm or less, and can be manufactured by physical crushing, but also can be manufactured by reducing metal ions or forming the complexes of metal ions, and agglomerating the metal ions or agglomerating the complexes as it is. Hereinafter, each time the metal nano-particle is mentioned, the metal nano-particle represents a metal particle or cluster having a particle diameter of 100 nm or less, and includes not only a metal nano-particle produced by reducing and agglomerating metal ions but also a cluster produced by agglomerating metal ions through a dispersant. As a method of adjusting metal nano-particles, a chemical method in which metal ions are reduced, transformed into metal atoms and metal clusters, and adjusted to nano-particles (by Kanjiro Torigoe and the like, Catalyst, 41521 (1999)) and other physical methods (JP-A-3-34211 and JP-A-5-98195) are known. In particular, it is difficult to physically manufacture nano-particles of several tens of nanometers or less. Therefore, it is preferable for example, to electrolyze a metal electrode so as to form ions, and agglomerate the ions, thereby manufacturing nano-particles as clusters. Particularly, "nanocluster" refers to a collection in which several to several hundreds of atoms and molecules collect, and the size reaches several nanometers to several tens of nanometers.

The metal nano-particle or cluster is selected from a group consisting of metal, gold, silver, and alloys thereof having SERS activity, and the diameter of the particles or cluster is preferably 50 nm to 5 nm and 20 nm to 5 nm in order to form the hot spot. In the double balloon of silver nano-particles, a phenomenon in which the location of the peak becomes higher as the particle diameter increases is also observed, but it is considered that a small particle diameter is more advantageous in the sense of the number of hot sites per unit area is formed between particles or at the front end of the edge shape. In addition, the shape of the nano-particle or cluster is generally a spherical shape, but may be deformed so that the number of hot sites per unit area is consequently increased according to the dimensions of the particle.

It is preferable to add a coordination compound which supplies ligands that form metal ions and metal complexes to a dispersed liquid of metal ions since the agglomeration size of the cluster can be easily adjusted. It is possible to form a dispersed liquid by forming the coordination compound and metal clusters of an appropriate size by adjusting the concentration of the coordination compound. In addition, when the coordination compound is a silver ion, coordination compounds having an amino group, such as ammonia, aliphatic amine, and amino acid, are known. A particularly preferred coordination compound includes amphoteric surfactants including an amino acid-based surfactant having an amino group and a carboxyl group, and, among them, addition of 0.001% by weight to 0.002% by weight of L-alanine, which is an amino acid-based surfactant, can form a silver ion solution into nano-clusters in which agglomeration of silver ions reaches 5 nm to 20 nm.

On the other hand, the metal substrate is determined by the kind of the metal nano-particle, and the metal nano-particle is selected from gold, silver, copper, and alloys thereof so that the electrode potential is decreased. The substrate does not need to be fully metal, and simply needs to have at least a metal surface showing a potential in a dispersed liquid. Therefore, for example, as shown in FIG. 7A, the metal substrate can be manufactured by punching a circle shape on a glass or plastic plate 1 and attaching an approximately 0.1 mm-thick dish-shaped metal plate 2. Since this substrate has the metal portion 2 formed into a dish shape, when the dispersed liquid is dropped, the dispersed liquid turns into droplets 3 and swells (FIG. 7B). After that, when the droplets are blown off using nitrogen-blowing or the like, agglomerated regions 4 of the metal nano-particles are formed on the metal surface so as to produce a measuring substrate. The potential of the metal substrate can be prepared by using an alloying technique, such as a gold alloy, silver alloy, and copper alloy, and adjusting the composition ratio. In addition, it is also possible to adjust the composition ratio by loading an appropriate degree of voltage. Meanwhile, agglomeration rate and the degree of agglomeration are important since they affect detection timing and inter-particle distance, respectively. This is because, according to tests in the double balloons of gold particles having a diameter of 40 nm, a resonance phenomenon due to surface plasmons occurs at a particle interval of 10 nm or less, and can be increased as the interval is decreased to 1 nm. In addition, the detection sensitivity as well as the duration is increased during the agglomeration of silver nano-particles, and, in a transient period which starts at the beginning of agglomeration from a decrease in the detection sensitivity and ends when agglomeration is completely finished, an optimal agglomeration interval due to a resonance phenomenon caused by the surface plasmons is exhibited, and a detecting peak is observed. Meanwhile, sometimes, it is preferable that the metal surface of the substrate used in the invention be oxidized since the agglomeration rate of the metal nano-particles can be adjusted. Therefore, there are cases in which it is preferable that an oxide be formed on the metal surface when the metal nano-particle dispersed liquid including a specimen is dropped on a substrate having the metal surface.

As described above, the metal substrate is selected in consideration of the electrode potential in the relationship with the metal nano-particles or clusters of an agglomeration target, but it is preferable to select a copper alloy plate, such as a copper plate, a brass plate, and a phosphor bronze plate, to agglomerate silver nano-particles or clusters. When this silver nanocluster dispersed liquid is agglomerated on the metal substrate, it is considered that clusters having SERS activity form crystals on the metal substrate together with ligands (FIG. 5), and agglomerated regions appropriate for the production of hot sites are formed.

The content of the metal nano-particle or cluster is 5000 ppm to 100 ppm, and particularly preferably 3000 ppm to 500 ppm. In the case of a high concentration, since the inter-particle density is high, formation of hot sites becomes fast (when the dispersed liquid included 0.001% by weight to 0.002% by weight of L-alanine, agglomeration durations of 6 minutes at 1000 ppm, 3 minutes at 2000 ppm, and 1 minute at 3000 ppm were appropriate), and therefore the agglomeration can be stopped early. In the case of a low concentration, since formation of hot sites is delayed, stoppage of the agglomeration is delayed. Therefore, in general, while an appropriate duration is set after the start of agglomeration, since the agglomeration state which acts as the hot site is affected by the content of the metal nano-particles or clusters in the dispersed liquid, the dispersant, the electrode potential difference with the substrate metal, and the like, it is important to determine the optimal conditions in advance.

Since the invention is to provide a method of measuring surface enhanced Raman scattered light in which the above measuring substrate is used so as to measure a variety of Raman scattered light, the invention is to provide a method of measuring surface enhanced Raman scattered light including a process in which agglomeration of a dispersed liquid including nano-particles (including clusters), which have a particle diameter of 100 nm or less, of a metal having a surface enhanced Raman activity function is stopped at an appropriate timing on a substrate having a metal surface having an electrode potential lower than the metal electrode potential of a metal having a surface enhanced Raman activity function after the start of the agglomeration, thereby providing optimally agglomerated regions, a process in which a detection specimen is attached to the metal agglomerated regions, and a process in which predetermined laser light is irradiated on the detection specimen adsorbed to the surface of the metal nano-particles in a non-dried state, and Raman scattered light generated from the detection specimen is measured.

A variety of disease markers or a variety of viruses are protein molecules, and absorption of protein molecules in optimal hot sites is a condition to use surface plasmon resonance (Surface). The present inventors found that, when an amino acid-based surfactant is used so as to form a dispersed liquid of silver nano-particles or clusters, the silver nano-particles are agglomerated on a metal substrate through an amino acid, and, consequently, the amino acid on the substrate can be electrostatically charged by charges that easily adsorb the protein molecules when the amino acid is treated using a solution with a pH at the isoelectric point or more or less. Therefore, the invention is to provide a method of measuring surface enhanced Raman scattered light in which an amphoteric electrolyte having at least an amino group and a carboxyl group in a dispersed liquid including 100 ppm to 5000 ppm of clusters of gold or silver nano-particles having a particle diameter of 5 nm to 100 nm is dispersed, the dispersed liquid including the amphoteric electrolyte is dropped on a metal substrate, agglomeration is started by the electrode potential difference between the metal substrate and the nanometal, the agglomeration is stopped in an optimally agglomerated state, then the amphoteric electrolyte is treated using a pH solution having the isoelectric point or more or less so as to be positively or negatively electrostatically charged, whereby a protein detection specimen is adsorbed, laser light is irradiated on the gold or silver nano-particles, and Raman scattered light generated from the adsorbed protein detection specimen is measured.

In the invention, the electrolyte is an amino acid-based surfactant or a protein-based surfactant, and is preferably an amino acid-based electrolyte having one or more amino groups with respect to a carboxyl group, such as glycine, L-alanine, and lysine. This is because the amino group is advantageous for the absorption of silver nano-particles. In addition, this is because it is easy to selectively adsorb charges with the protein molecules that are electrostatically charged positively or negatively since amino acid is electrostatically charged positively by a treatment of a pH solution having the isoelectric point or more, and electrostatically charged negatively by a pH solution having the isoelectric point or less.

Particularly, when an antigen-antibody complex reaction is used, the metal nano-particle dispersed liquid used in the invention is preferably a protein-based surfactant including an amino acid-based amphoteric surfactant as the surfactant, and the surfactant is considered to be interposed between the agglomerated metal nano-particles so as to play a role of inducing an antibody component or an antigen component between the metal nano-particles. It is preferable to select from and singly add the antibody component or jointly use and add an amino acid-based electrolyte and the antibody component.

According to the invention, since it is possible to form an optimally agglomerated form on a metal substrate by using an amphoteric electrolyte in a dispersed liquid, and also possible to selectively form charges necessary for protein adsorption by using the properties of the amphoteric electrolyte, protein adsorption can be reliably carried out. Furthermore, in the invention, since adjustment of the intervals of metal nano-particles or clusters can be controlled by the agglomeration duration, it is possible to adsorb protein molecules in the optimal hot spots. Therefore, SERS detection of a variety of protein molecules can be detected with favorable reproducibility, and detection of each disease marker and a variety of viruses becomes possible.

In the invention, a variety of dispersing agents can be used as the metal nano-particle dispersed liquid, but it is necessary to select a dispersant so as not to form noise of a detection specimen. The agglomeration prevention effect, such as the concentration of a dispersant, should be considered so that the optimal detection timing can be set in consideration of the relationship with a colloid metal and the electrode potential of a metal substrate. Therefore, the invention is a dispersed liquid used in the above measuring method, and is to provide a metal nano-particle dispersed liquid having a surface enhanced Raman activity function obtained by adding a coordination compound that supplies ligands to metal ions to a dispersed liquid of metal ions having a surface enhanced Raman activity function and forming metal complex clusters.

The coordination compound is preferably an amphoteric surfactant including an amino group and a carboxyl group in the case of protein detection, and is supposed to be a dispersed liquid to which the antibody component of the antigen-antibody complex reaction is added singly or together with the amphoteric surfactant when an antigen-antibody complex reaction is used. When the amphoteric surfactant is a protein-based surfactant including an amino acid-based surfactant, the amphoteric surfactant has a function of inducing the antibody component or the antigen component between the metal nano-particles or clusters.

DESCRIPTION OF EMBODIMENTS

The embodiments of the invention will be described in detail with reference to the following drawings.

Example 1

Figure 1:
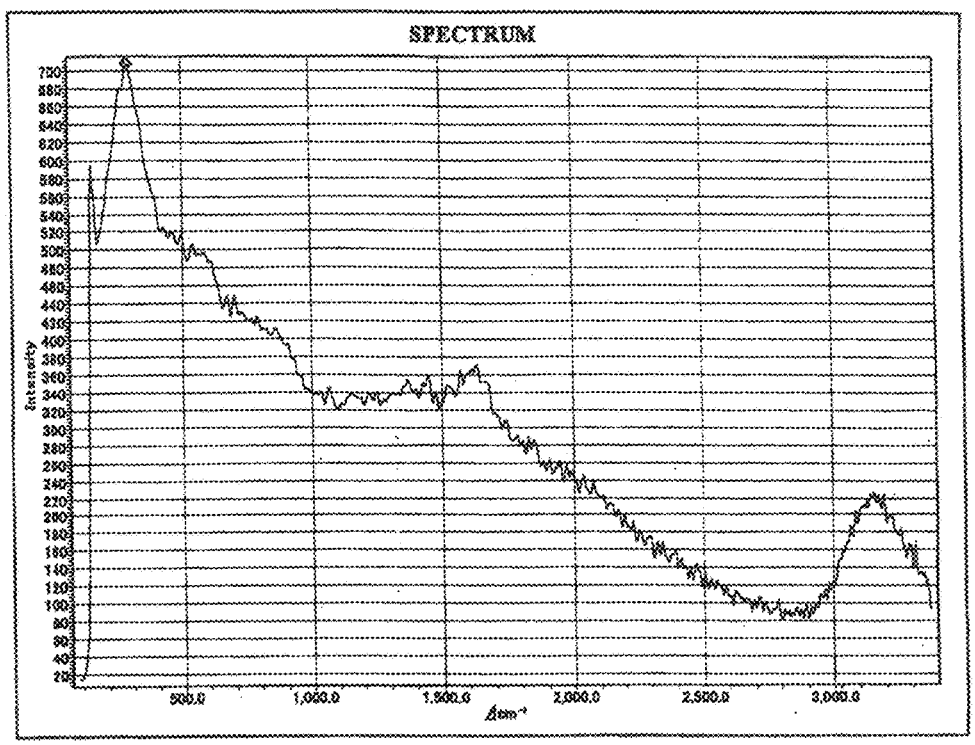
FIG. 1 is a background spectrum of a substrate having no 4,4'-bipyridine in the substrate for which the agglomeration duration is 6 minutes.
Figure 2:
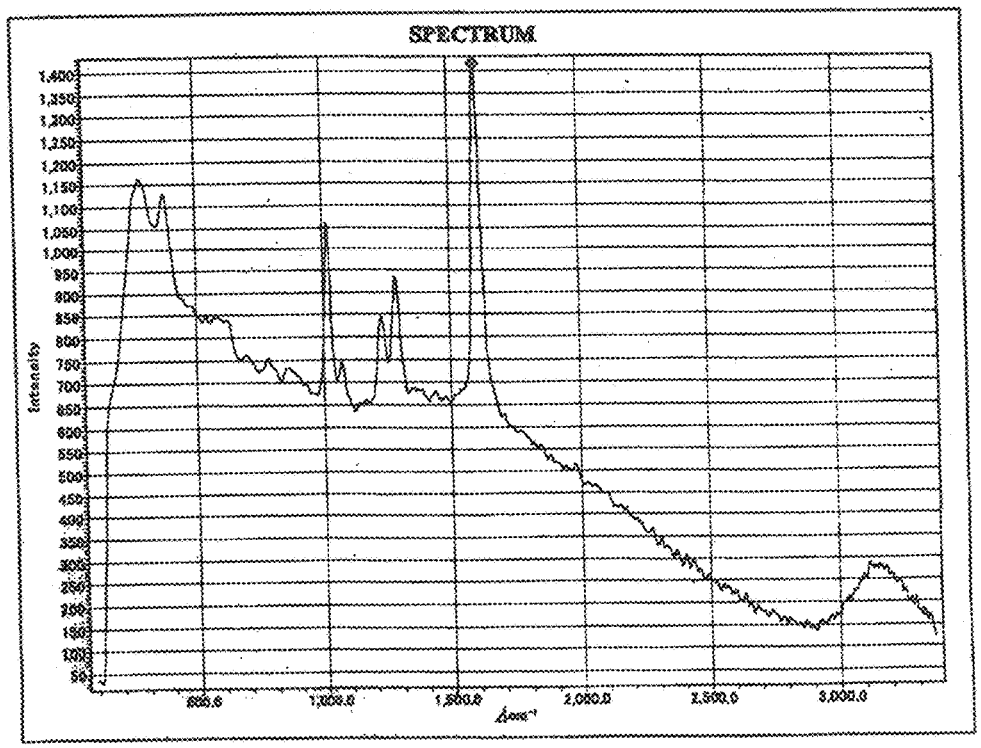
FIG. 2 is a SERS spectrum of 1 μM of 4,4'-bipyridine in the substrate for which the agglomeration duration is 7 minutes.
Figure 3:
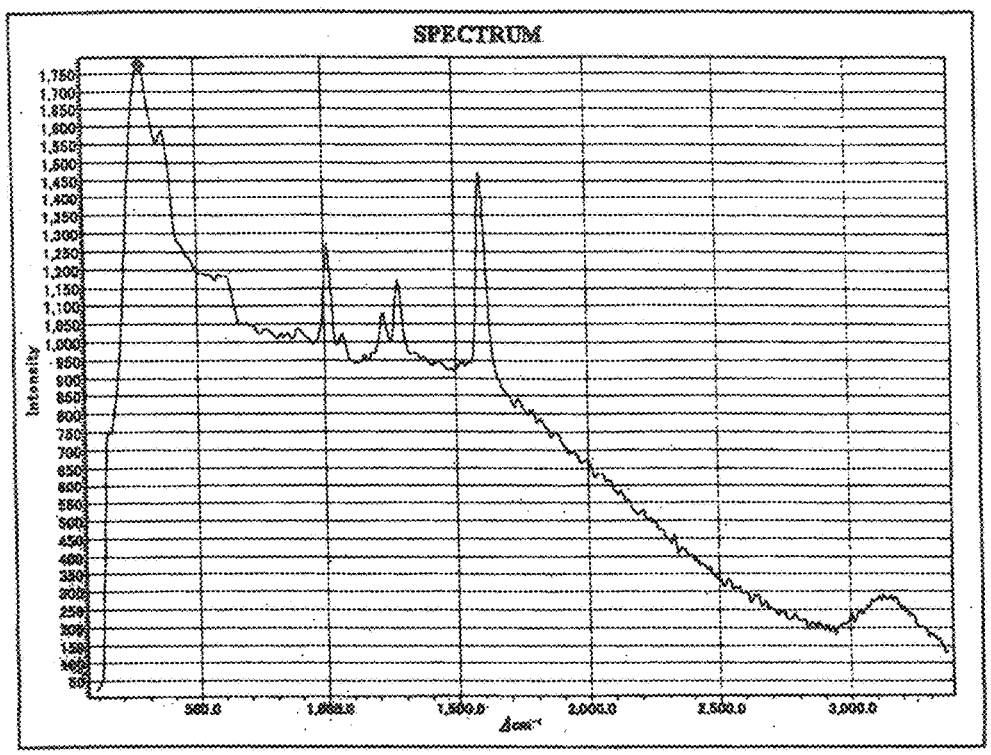
FIG. 3 is a SERS spectrum of 1 nM of 4,4'-bipyridine in the substrate for which the agglomeration duration is 6 minutes.
Figure 4:
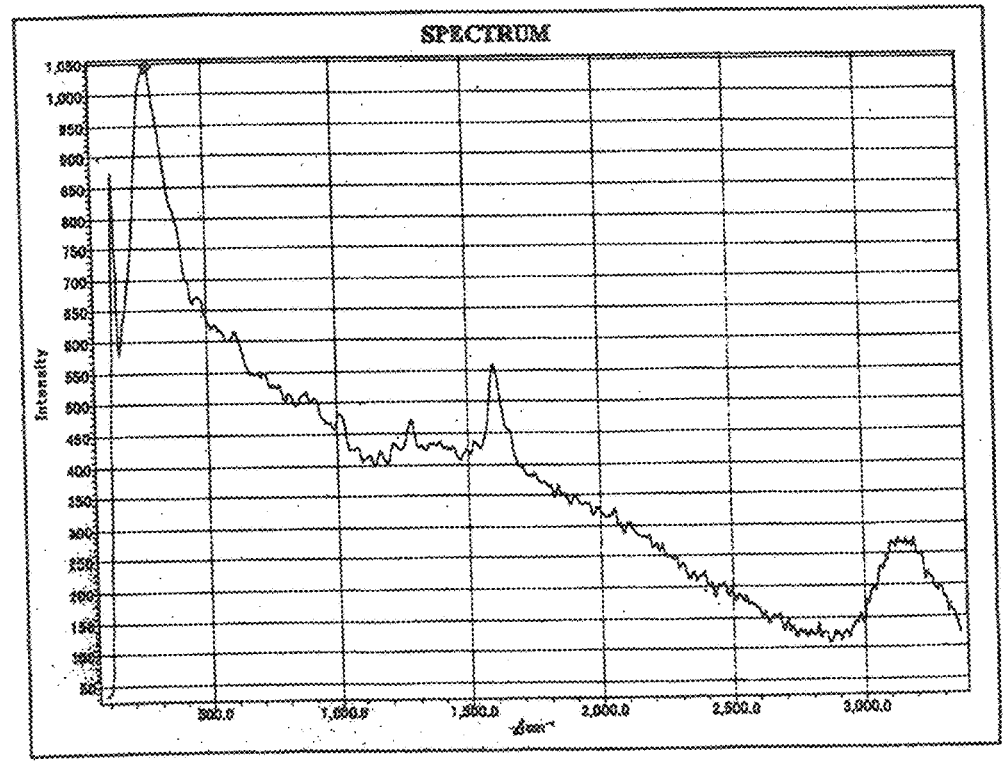
FIG. 4 is a SERS spectrum of 1 nM of 4,4'-bipyridine in the substrate for which the agglomeration duration is 7 minutes.

In the present embodiment, silver nanoclusters having an average particle diameter of 7 nm to 10 nm, which had been produced by a method in which silver ions were agglomerated by a chemical method, were dispersed in an aqueous solution including an amino acid-based dispersant composed of L-alanine, thereby producing 2000 ppm, 1000 ppm, and 100 ppm silver nanocluster dispersed liquids (colorless and transparent). Droplets (10 μL) of 1000 ppm of the dispersed liquid were dropped one by one at intervals on each of surface-cleaned silver substrate, copper plate, and brass substrate, and the agglomeration process was observed. While it took almost one night for the dispersed liquid to be agglomerated on the silver substrate, black deposits were formed on the copper substrate from several minutes, and on the brass bronze substrate from several tens of seconds to several minutes. Here, the agglomeration was stopped by carrying out nitrogen-blowing 6 minutes and 7 minutes after dropping so as to scatter and dry water droplets. 4,4-bipyridine was diluted in 1 μM and 100 nM of pure water, and dropped on the deposited regions on the 6-minute agglomerated and 7-minute agglomerated brass substrates that were produced in the above manner, and SERS spectra were measured using a measuring device, manufactured by Ramada Co., Ltd., and laser having a wavelength of 825 nm at the maximum output as excited light. The results are shown in FIGS. 1 to 4. FIG. 1 is a spectrum when pure water was dropped on the 6-minute agglomerated substrate. FIG. 2 is a SERS spectrum when 1 mM of 4,4'-bipyridine was dropped on the 7-minute agglomerated substrate. FIGS. 3 and 4 are SERS spectra when 1 nM of 4,4'-bipyridine was dropped on the 6-minute agglomerated substrate and the 7-minute agglomerated substrate, respectively.

When the spectra in FIG. 1 and FIGS. 2 to 4 are compared, it is found that the specimens having concentrations of 1 μM and 100 nM can be measured. In addition, it can be understood from the comparison between FIGS. 3 and 4 that the 6-minute agglomeration is better than the 7-minute agglomeration, and there is an optimal agglomeration duration.

According to such measuring substrates, when the focusing of laser light was completed, the SERS spectrum of 100 nM of 4,4'-bipyridine could be detected instantly by dropping a predetermined specimen in agglomerated regions on the substrate.

Example 2

Figure 5:
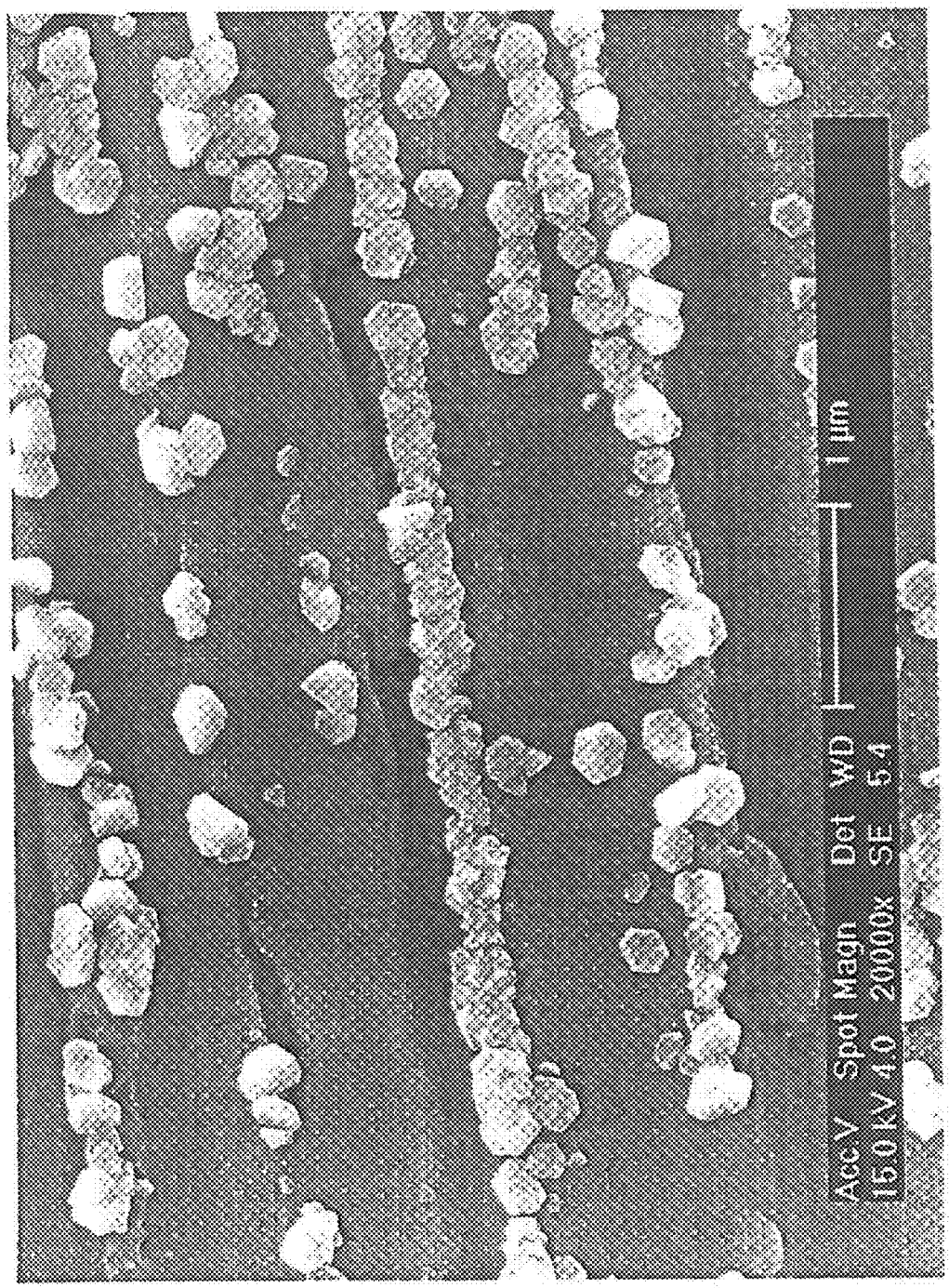
FIG. 5 is a 20,000 time-magnified SEM photograph of a state in which a silver nano-particle dispersed liquid including an electrolyte is agglomerated on a phosphor bronze substrate.
Figure 6:
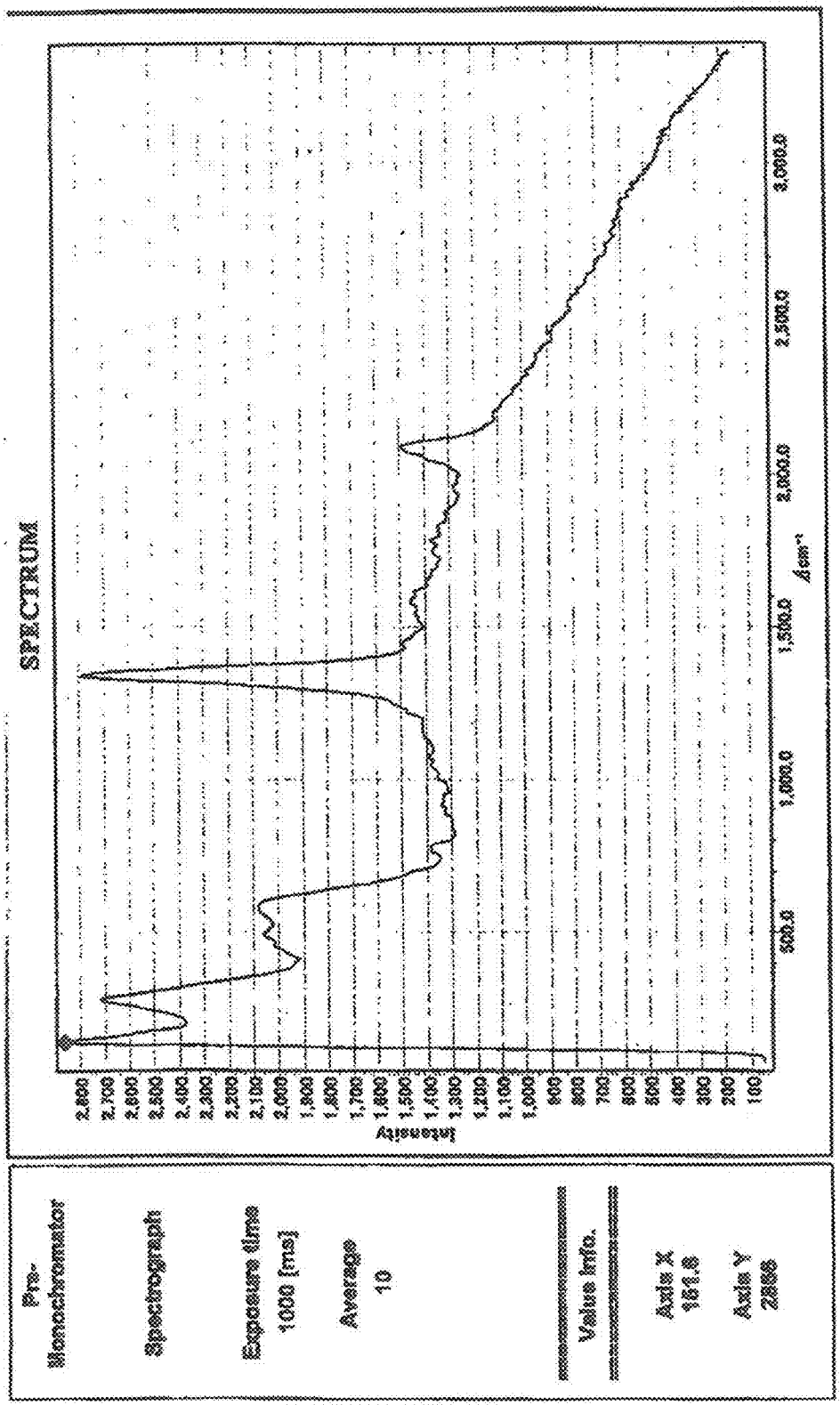
FIG. 6 is a SERS spectrum of the CRP measured in Example 2.
Figure 7A:
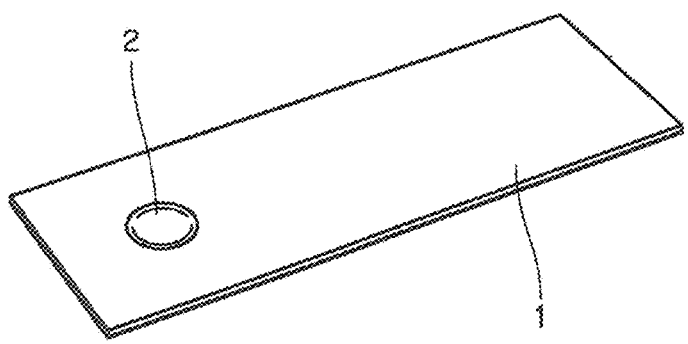
FIG. 7(a) is a process chart showing the process of manufacturing the measuring substrate according to the invention.
Figure 7B:
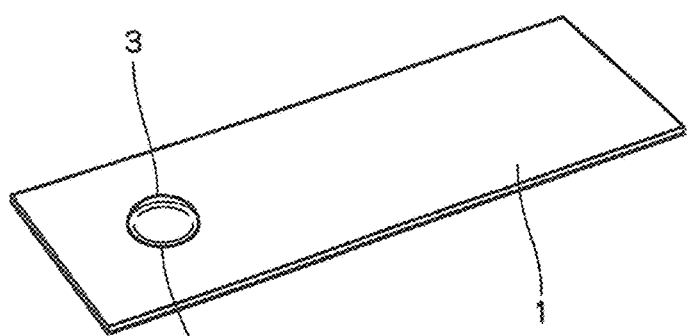
FIG. 7(b) is a process chart showing the process of manufacturing the measuring substrate according to the invention.
Figure 7C:
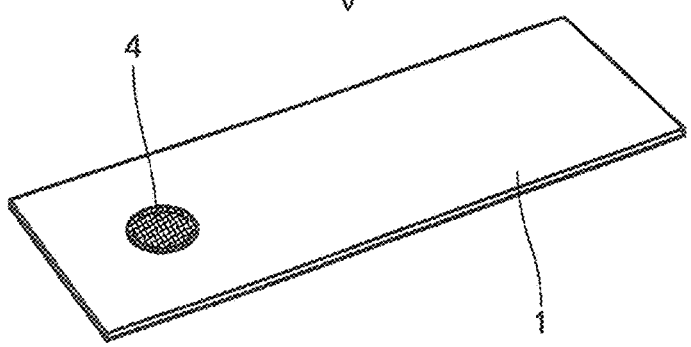
FIG. 7(c) is a process chart showing the process of manufacturing the measuring substrate according to the invention.

The silver nano-particles or clusters having an average particle diameter of 7 nm to 10 nm, which were used in Example 1, were dispersed in an aqueous solution including an amino acid-based surfactant (0.001% to 0.002% of L-alanine), thereby producing 2000 ppm, 1000 ppm, and 100 ppm silver nano dispersed liquids (colorless and transparent). Droplets (10 μL) of 1000 ppm of the dispersed liquid were dropped one by one at intervals on each of surface-cleaned silver substrate, copper plate, and brass substrate, and the agglomeration process was observed. While it took almost one night for the agglomeration on the copper substrate, black deposits were formed on the brass substrate from several minutes, and on the phosphor bronze from several tens of seconds to several minutes. Here, the agglomeration was stopped by carrying out nitrogen-blowing after the dropping so as to scatter and dry water droplets. CRP (1000 times the ordinary concentration) was diluted in pure water into 10 times and 100 times, dropped on the deposited regions on the 6-minute agglomerated phosphor bronze plate produced in the above manner (the SEM photograph shown in FIG. 5), and SERS spectra were measured using a measuring device, manufactured by Ramada Co., Ltd., and laser having a wavelength of 825 nm at the maximum output as excited light. The results are shown in FIG. 6.

INDUSTRIAL APPLICABILITY

According to the invention, it is possible to provide a measuring substrate that can measure SERS light immediately after a detection specimen is dropped. In addition, since use of such a measuring substrate can adjust the charge state in optimally agglomerated regions which act as hot sites, absorption of protein in nano-particles, which is necessary to detect protein, becomes easy. In addition, measurement for diagnoses of diseases and the like by detecting cancer markers and viruses also becomes possible by using an antigen-antibody complex reaction.

The invention claimed is:
1. A metal substrate used for surface enhanced Raman scattered light measurement, comprising
   an agglomerated region of metal nano-particles having SERS activity selected from the group consisting of Au and Ag on the metal substrate selected from the group consisting of Cu or Cu alloy, wherein the Cu or Cu alloy substrate has a lower or base electrode potential in a liquid than that of Au or Ag nano-particles having a particle diameter of 100 nm or less, wherein the Au or Ag nano-particles can be electrochemically deposited directly on the Cu or Cu alloy substrate to form Au or Ag nano-particle agglomerates on the Cu or Cu alloy substrate from the liquid dispersed with 100 to 5000 ppm of the Au or Ag nano-particles by means of the electrode potential difference between the electrode potential of the Cu or Cu alloy and that of the Au or Ag particles in the liquid and the agglomeration can be stopped in a desired agglomerated state by blowing off the liquid on the Cu or Cu alloy substrate, wherein the Au or Ag nano-particle agglomerates are crystalline.

2. The substrate used for surface enhanced Raman scattered light measurement according to claim 1, wherein the liquid dispersed with Ag as the metal having SERS activity contains a coordination compound that supplies ligands provided with an ability of forming a metal complex with silver ions in the liquid.

* * * * *